United States Patent [19]

Duncan et al.

[11] Patent Number: 5,616,184
[45] Date of Patent: Apr. 1, 1997

[54] SOLUTION REMOVAL NOZZLE

[75] Inventors: Gregory S. Duncan; Olin W. Calvin; Mark E. Schlagel; Darren S. Keene; Russell J. Edwards, all of Jacksonville, Fla.

[73] Assignee: Johnson & Johnson Vision Products, Inc., Jacksonville, Fla.

[21] Appl. No.: 617,304

[22] Filed: Mar. 18, 1996

Related U.S. Application Data

[63] Continuation-in-part of Ser. No. 999,234, Mar. 29, 1993, abandoned.

[51] Int. Cl.$^6$ .................................................... B08B 3/02
[52] U.S. Cl. .................... 134/22.1; 134/186; 134/169 R; 134/901; 15/302
[58] Field of Search .................... 134/155, 186, 134/102.2, 166 R, 169 R, 177, 201, 182, 183, 175, 167 C, 166 C, 901; 206/5.1; 15/302, 304, 322, 320, 345; 34/224; 134/22.1, 22.12, 24, 25.4

[56] References Cited

U.S. PATENT DOCUMENTS

| | | | |
|---|---|---|---|
| 1,854,471 | 4/1932 | Hofmann | 15/304 |
| 2,538,366 | 1/1951 | Kerwin | 134/172 |
| 3,545,458 | 12/1970 | Korb et al. | 134/901 |
| 3,849,830 | 11/1974 | Wagner | 15/302 |
| 3,990,579 | 11/1976 | Manning | 134/901 |
| 4,053,284 | 10/1977 | Posch | 15/304 |
| 4,341,568 | 7/1982 | Christensen | 15/304 |
| 4,635,665 | 1/1987 | Namba et al. | 134/167 R |
| 4,675,067 | 6/1987 | Valley | 134/186 |
| 4,733,428 | 3/1988 | Malinge et al. | 15/302 |
| 4,784,167 | 11/1988 | Thomas et al. | 134/901 |
| 4,986,290 | 1/1991 | Oguma et al. | 134/901 |
| 5,080,839 | 1/1992 | Kindt-Larsen | |
| 5,094,609 | 3/1992 | Kindt-Larsen | |
| 5,158,101 | 10/1992 | Sakka | 15/302 |
| 5,175,159 | 1/1993 | Yoshihara et al. | 134/186 |
| 5,176,126 | 1/1993 | Tanaka et al. | 134/901 |
| 5,195,549 | 3/1993 | Adams | 134/901 |

FOREIGN PATENT DOCUMENTS

| | | | |
|---|---|---|---|
| 3-287117 | 12/1991 | Japan | 134/901 |
| 3-284721 | 12/1991 | Japan | 134/901 |

Primary Examiner—Frankie L. Stinson

[57] ABSTRACT

An apparatus and a method for removing a liquid from a container having a bowl and a flange, the bowl holding the liquid and containing a hydrophilic ophthalmic lens, wherein there is provided a nozzle with a central face and a shoulder around the periphery of the face. The shoulder has a sealing means which is sized to fit on the flange of the container, where it forms a sealed volume above the container bowl, this volume including the volume of the bowl itself. The central face has through it at lease one fluid entrance passage and at least one fluid exit passage arranged so that the flow is distributed substantially symmetric about the center axis of the lens. The apparatus includes a lens retainer which resiliently urges the lens into engagement with the bowl so that when the purging fluid is introduced into the sealed volume, there is no migration of the lens. There is connected to the entrance passage a source of purging fluid that has a pressure and flow sufficient to remove substantially all the liquid through the exit passage.

20 Claims, 3 Drawing Sheets

SOLUTION REMOVAL NOZZLE

CROSS REFERENCE TO RELATED APPLICATIONS

This application is a continuation-in-part of applicant's prior patent application U.S. Ser. No. 07/999,234 entitled SOLUTION REMOVAL NOZZLE, filed Mar. 29, 1993, now abandoned.

BACKGROUND OF THE INVENTION

This invention relates to a method and apparatus for removing processing liquid from a lens-bearing container during manufacture of molded ophthalmic lenses. This invention is suited to molded ophthalmic lenses such as hydrogel contact lenses, although the method is also suitable for other hydrophilic, high-precision ophthalmic lenses such as intraocular lenses. In particular, this method and apparatus are directed to the removal of deionized water from an ophthalmic lens package after lens inspection, and immediately prior to saline dosing and package sealing.

As the ophthalmic lens industry has grown, and in particular the industry related to supplying contact lenses that are provided for periodic frequent replacement, the number of lenses that need to be produced has increased dramatically. This has required manufacturers to strive for methods and apparatus that can be adapted to automated practices and perform with consistency.

Similarly, the promise of easier insertion of a folded or rolled intraocular lenses through a smaller incision has increased the interest in soft intraocular lenses for patients undergoing cataract removal and lens replacement. Soft ophthalmic lenses for placement on the cornea or within the eye, such as contact lenses or soft intraocular lenses, can be made by a variety of techniques. Ophthalmic lenses can be made by spin casting a monomer material in a rotating mold then polymerizing the material so shaped. Another method used to manufacture both contact lenses and intraocular lenses in precision lathing of a piece of material which is then polished and used as a lens.

Recently the molding of soft contact lenses and soft intraocular lenses has come into favor. This technique has the advantages of repeatability and speed that compares favorably with the prior methods of manufacturing lenses, such as by forming a monomer or monomer mixture in a mold such as one mad polystyrene or polypropylene.

Techniques for successfully molding such lenses can be found in U.S. Pat. Nos. 4,495,313 and 4,640,489 to Larsen and U.S. Pat. Nos. 4,889,664; 4,680,336 and 5,039,459 to Larsen et al. These patents specifically described the use of a diluent, a material which substitutes for water during the molding process, and which is replaced with water after the molding has been completed. The advantage of this technique is that the optical properties, size and shape of the lens thus made does not change as radically as with methods that do not utilize such diluent.

It is further known in the art to mold such ophthalmic lenses by forming a monomer or monomer mixture in a mold such as one made form polystyrene or polypropylene.

An example of this art can be found in U.S. Pat. No. 4,565,348 to Larsen. In contrast to the above polystyrene molds, another example is the use of polypropylene or polyethylene molds such as that described in U.S. Pat. No. 4,121,896 to Shepherd.

A practical method and apparatus for mass production of molded contact lenses using the above described processes is given in U.S. Pat. Nos. 5,094,609 and 5,080,839 both to Kindt-Larsen. Although the method and apparatus described therein are specifically directed to the removal of the diluent from the polymerized lens after molding and replacement with water, there is described in general the process steps that must be undertaken subsequent to the removal of the diluent and hydration of the lens.

In the U.S. Pat. No. 5,080,839 patent there is shown in FIG. 1 at element 130 a step described as deionized water removal. This removal is shown as taking place in an inspection carrier or final package. Subsequent steps are shown as saline deposition and sealing of the package.

The method and apparatus described in the above patents represents an improvement in the lens hydration process in that only deionized water is used for hydration, that is, release of the lens from the mold and hydrolysis of the diluent, instead of the performing the solution exchange operation with saline solution in a tank batch process. While this method has the benefits of no salt usage representing a cleaner and less corrosion prone system and accelerating processing times due to the deferment of meth-acrylic acid neutralization, it requires that the lens be transferred from the deionized water to a saline system so the lens can equilibrate to its final properties. Further because the inspection process is done in the primary package, it is necessary to exchange the deionized water with saline solution with the lens in the package and without removing the lens.

In the '839 patent it is stated that the deionized water is removed from the recesses of the inspection carrier and replaced with a saline solution which has a pH and osmolality compatible with the tears of the human eye. It is stated that alternately an aliquot of concentrated brine solution may be added to the deionized water such that the final solution has the same pH and osmolality mentioned above. Saline solution is used so that when the user removes the lens from the package, ready to insert the lens on the cornea of the eye, the pH and osmolality of the lens will be balanced with that of the eye and the lens will not irritate the eye when inserted. If the material from which the lens is made has an ionic characteristic, the salts in the saline solution will neutralize that ionic species. The neutralization can be done in the final package on the shelf outside the remainder of the manufacturing process. It may also be possible therefore to insert a small portion of solid sodium chloride salt into the ionized water to allow this stabilization to occur in the package after sealing.

Two considerations, however, make this approach impractical; first, the overall process requires a high degree of accuracy and repeatability. This is particularly difficult do to the small volume of the package cavity which is approximately 1 ml, and wherein a significant percentage in salinity. The direct addition then of either concentrated saline solution or solid sodium chloride salt would result in a significant variation and in final solution concentration.

The second problem with any attempt to partially remove the deionized water and replace it with concentrated saline is the handling of salt solution. As is well known, sodium chloride is corrosive to many materials and represents processing problems such as salt crystal build-up after evaporation causing faulty seals, which is best avoided.

Great difficulties were encountered in achieving complete water removal by various methods. One such method was the insertion of a needle into the lens container to withdraw water. Experimentation with this method resulted in a repeatability for the six sigma range of 60 mg, which is approximately equal to a variability of 6% dilution of the final packing solution. Another method was the tilting of the package. In both instances, the amount of water on the remaining in the package afterward was variable and could not be relied upon to give the appropriate salinity with the addition of concentrated saline. A second problem with the tilting method is the presence of water of the remainder of the package interfering with final package sealing. Other methods to induce removal of the water in vapor form, such as microwave-induced evaporation, are too slow.

It was an object of the invention described in the parent application to provide a method and apparatus that could quickly and completely remove the deionized water form the lens container. While in large part this apparatus was successful, it was found that in a small percentage of cases, particularly if the lens was not initially well centered, the lens would be dislocated by the jet of air, and slide to the side of the bowl, or onto the nozzle face, and then be dislodged from the package during subsequent material handling. This created, over a period of time, when several lenses had been dislodged, and partially dried by air, a sticky debris which had the ability to create equipment malfunctions, and expensive downtime for the entire line, while the missing, and largely transparent, lenses were located and cleaned from the system. While the error rate was quite small, and less than 1%, the downtime was unduly expensive when the line as a whole was producing several thousand lenses an hour.

It is a further object of the present invention to perform such deionized water removal with a higher success rate, without damaging or altering the final physical properties of the lens.

It is another object of the present invention to provide a method of establishing a final solution concentration that is highly accurate and repeatable so that the lens equilibrates to the proper oslmality.

It is a final object of the invention to provide a method and apparatus that achieves the above objects in such a controlled manner that the liquid is not distributed elsewhere so that moisture interferes with the subsequent sealing of the package.

SUMMARY OF THE INVENTION

The above objects are achieved and problems overcome with an apparatus and a method for removing a liquid from a container having a bowl and a flange, the bowl holding the liquid and containing a hydrophilic ophthalmic lens, wherein there is provided a nozzle with a central face and a shoulder around the periphery of the face. The shoulder has a sealing means which is sized to fit on the flange of the container, where it forms a sealed volumes above the container bowl, this volume including the volume of the bowl itself. When sealed in this way, the central face is positioned above the lens within the bowl. The central face has through it at least one fluid entrance passage and at least one fluid exit passage. There is connected to the entrance passage a source of purging fluid that has a pressure and flow sufficient to remove substantially all the liquid through the exit passage. The lens is temporarily secured within the bowl by a resilient lens retainer while the purging fluid is removing the deionized water therefrom. The entrance passage and exit passages are arranged so that the flow is distributed substantially symmetric about the center axis of the lens and the retaining means so that when the purging fluid is introduced into the sealed volume, there is no migration of the lens.

In the preferred embodiment, the entrance passage is located along the central cylindrical axis of the nozzle with a plurality of exit passages located in symmetric arrangement between the central axis and the shoulder. The lens retaining means is an array of elastomeric nubs which urge the soft lens into contact with the bowl surface, and the preferred purging fluid is filtered air.

DESCRIPTION OF THE PREFERRED EMBODIMENT

Figure 1:
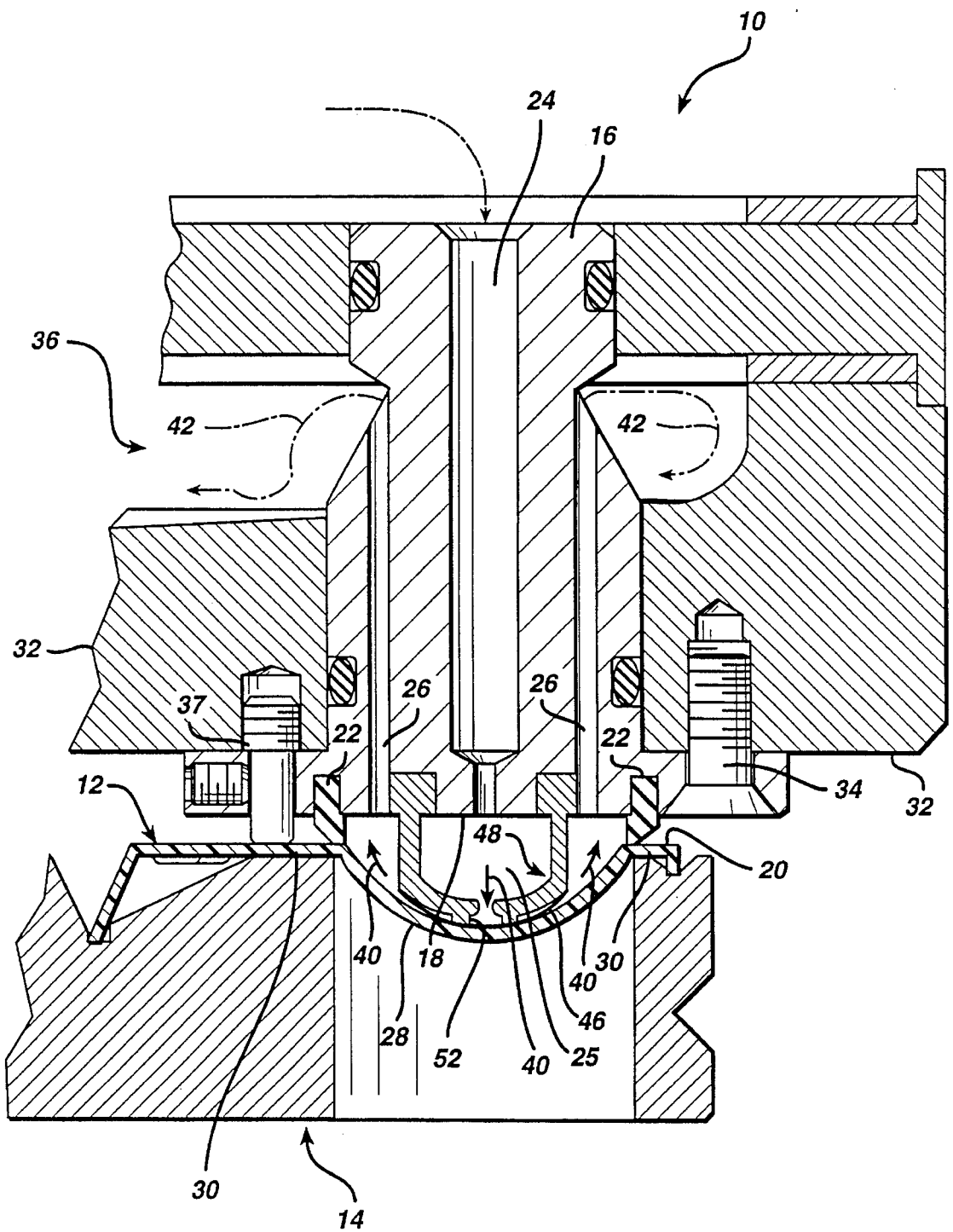
FIG. 1 is a cross sectional view of the apparatus of the present invention and lens retainer and shows as well the container which holds the liquid and ophthalmic lens.

Referring now to FIG. 1, there is shown the apparatus of the present invention 10 along with container 12 and container pallet 14, each of which has been magnified for clarity of expression. Solution exchange apparatus comprises solution exchange nozzle 16 having a central face 18 and shoulder 20. The nozzle also includes an entrance passage 24 and exit passages 26, while shoulder 20 has sealing means such as a silicon gasket 22.

While face 18 of the nozzle is shown as being flat, other shapes are acceptable, such as a tip in the center of the face which includes the entrance passage 24. Although this embodiment is acceptable and has certain advantages in retaining the lens in the container 12, it is not preferred because of positioning criticality and the possibility of snagging the lens.

Container 12 is generally comprised of a bowl portion 28 and a flange portion 30. A package design suitable for use with the apparatus of this invention and having properties compatible with obtaining the goals thereof is described in copending U.S. patent application Ser. No. 07/995,607 filed on Dec. 21, 1992 (attorney docket VTN-43) and entitled "Ophthalmic Lens Package".

Positioned within the bowl portion 28 of package container 12 is a soft ophthalmic lens 46, which is retained therein during evacuation by lens retainer 48. As will be hereinafter described in greater detail with respect to FIGS. 3–3B, the lens retainer 48 includes a plurality of nubs 52 which urge the lens into contact with the inner surface of bowl 28 during evacuation of fluids therein.

Because it is desirable to process more than one container at a time, nozzle 16 is located within assembly 32, to which it is secured by attachment means such as screws 34. Multiple nozzles can be connected in arrays, such as a 2×4, 2×8 or 4×8 array for continuous batch processing, and manifolds may be used to connect like entrance passages 24 or like exit passages 26 for each of the nozzles in the array to a manifold such as through manifold 36. A manifold for the entrance passage 24 is not shown.

The entrance passage is connected to a source of purging fluid such as a gas (purified air) or saline solution.

In order to prevent the solution removal apparatus 10 from having the package 12 adhere to the apparatus after liquid removal, a bias means, such as spring driven plunger 37, is provided to supply a separation force between the two.

Figure 2:
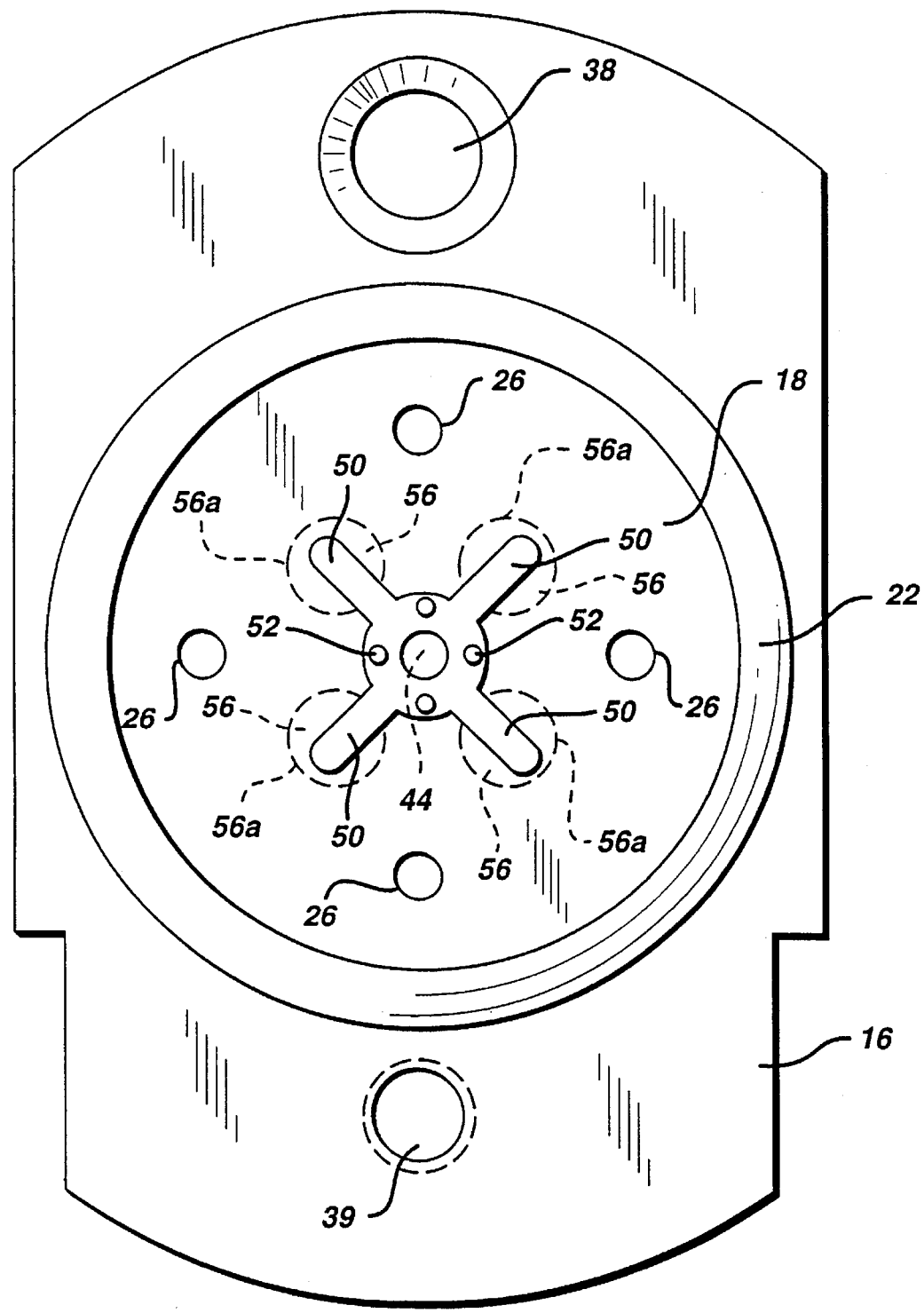
FIG. 2 is a bottom plan view showing the removal apparatus and retainer illustrated in FIG. 1.

Turning now to FIG. 2, nozzle 16 is depicted in a bottom plan view showing the surface of central face 18. Also shown is sealing means such as a silicon gasket 22, the lens retainer 48, and the body of nozzle 16. The gasket 22 conforms to the shape of the package surface, but preferably the gasket contacts from its interior edge first, in order to prevent liquid from contacting the package sealing area of the flange. Holes 38 and 39 are shown indicating the location where attachment means 34 and spring plunger 37 are provided to attach the nozzle to the body of assembly 32, and provide separation force, respectively.

Directing attention to face 18, there is shown an entrance passage 24 and four exit passages 26. As can now be more readily seen and appreciated, the entrance passage is located along the central axis of the nozzle 16 passing through the center of face 18. The exit passages 26 are also located symmetrically around entrance passage 24 between the center of face 18 and shoulder/sealing means 22. In addition, the nubs 52 of the lens retainer are also arranged symmetrically around the entrance passageway 24 between the center of face 18 and the sealing means 22. In this way, purging fluid provided through entrance passage 24 flows symmetrically through the sealed volume 25 and exits symmetrically through exit passages 26.

A specific embodiment achieving the objectives of this invention is defined by passages having a 0.062 inch diameter at the face. The entrance passage expands to 0.197 inches where it is connected to the purging fluid source. The diameter across the bowl and likewise the distance to the inner edges of sealing means 22, is 0.905 inches.

The central cylindrical axis of central passages 26 are located 0.310 inches from the center of the nozzle face 18. The purging fluid may be purified air or may be saline solution, which has the advantage of accomplishing deionized water removal and saline insertion in one step. The above described problems of handling a salt solution, however, are still present.

Two methods of providing the purging fluid at the proper pressure and flow rate are possible. The first is the application of the fluid, preferably sterile air or nitrogen, into the entrance passage at a relatively low pressure while sealing the nozzle by sealing means 22 against the flange 30 to create the sealed volume 25. This pressurizes the sealed volume and forces the deionized water out through the outlet holes as indicated by arrows 40. The liquid and purging fluid continue up passages 28 and exit through the manifold 36, as indicated by arrows 42.

The lens 46 is held on the bottom center of the cavity by the flow of purging fluid through the entrance passage 24 and the resilient action of lens retainer 48. The effluent is routed away from the fixture by tubing connected to the manifold 36 to avoid contact with the package flange. Surprisingly, the lens/package system is extremely robust to this operation, and in fact, the lens normally sticks to the package bowl by the surface tension of residual deionized water contained in the lens. As noted previously, in well over 99% of the evacuations, the lens remains centered in the package bowl, but in a low percentage of instances, particular when the lens is not initially well centered, the lens is blown from the center portion of the bowl, and as the nozzle is retracted, becomes separated from the bowl and becomes debris within the system, eventually requiring a shutdown of the line for cleaning and removal of the lenses.

Figure 3:
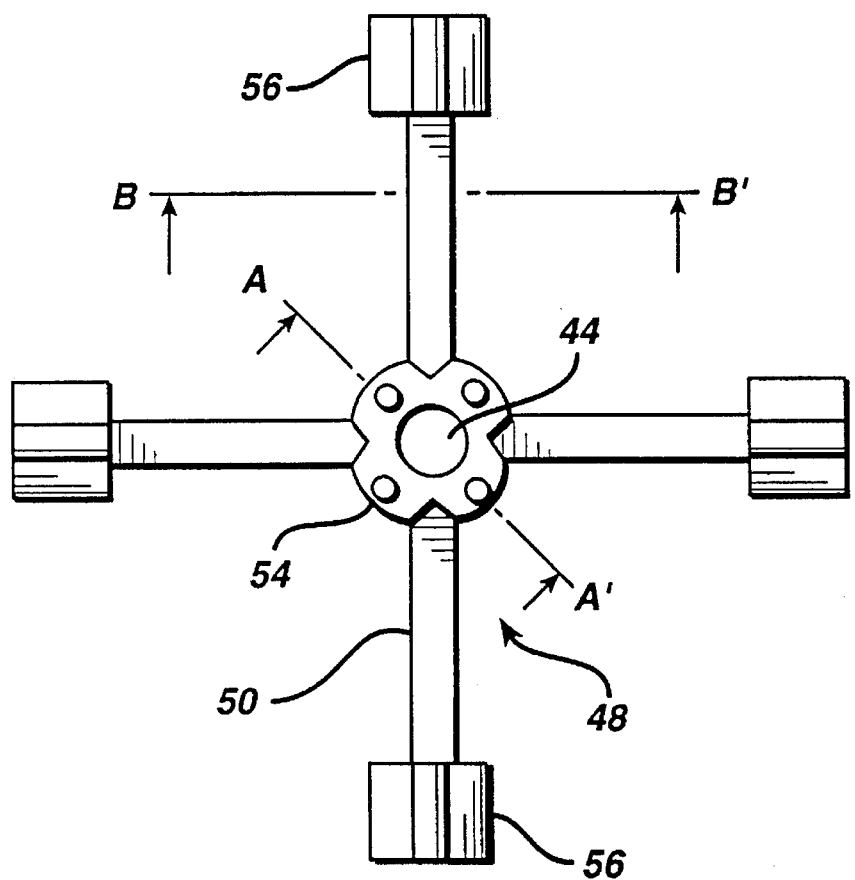
FIG. 3 is a plan view of the lens retainer prior to installation in the nozzle.
Figure 3A:
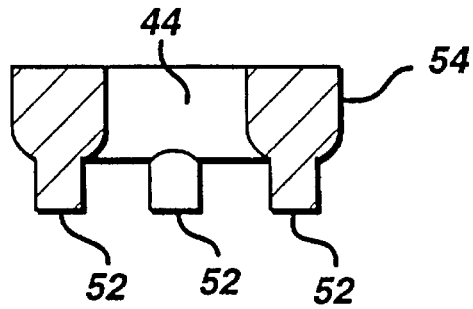
FIG. 3A is a cross section taken along section line A—A' of FIG. 3.
Figure 3B:
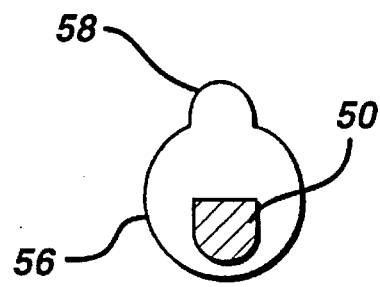
FIG. 3B is a cross section taken along section line B—B' of FIG. 3.

To affirmatively retain the lens in the bowl area, it has been found that a lens retainer, such as retainer 48, can be used to prevent inadvertent lens displacement. As illustrated in FIGS. 3–B, a lens retainer 48 is formed of a silicon elastomer, preferably having a durometer hardness of 70A. If desired, a small amount of iron oxide, up to 2 parts per 100, may be added for viability.

Lens retainer 48 is preferably formed in a symmetrical pattern, such as the four sided cross illustrated in FIG. 3, with a plurality of lens engaging nubs 52 mounted on hub 54. Hub 54 also includes a central opening 44, which when installed, will be coaxially aligned with orifice 24 of nozzle 16, as illustrated in FIG. 2. Each of the cross arms 50 is terminated with an anchor fitting 56 having a key 58 as illustrated in Figure b. The anchor fitting 56 and key 58 cooperate with an opening 56(a) and keyway formed in nozzle face 18 as illustrated in FIG. 2. The key 58 and related keyway prevents undesired twisting of the cross arms 50 during installation. The rounded lower portion of each cross arm 50 is slightly roughened by glass peening the mold cavity used to form the lens retainer 48.

During normal operation the only portions of the lens retainer that comes into contact with the lens are the nubs 52. The resilient load exerted by the nubs against the contact lens 46 is extremely light, by virtue of the diameter and length of cross arms 50 and the durometer hardness of 70A. Consequently, the retainer does not mar or damage the soft and newly polymerized lens. When the nozzle is retracted, the lens is retained in the bowl by virtue of the surface tension of the wetted lens against the bowl, and the ratio of respective surface areas of the ends of nubs 52 on one side, and the wetted surface of the lens touching the bowl on the other side.

After the cavity has been flushed with air, the nozzle is retracted, and the package container is advanced to other workstations for saline dosing and sealing. Alternately, the saline may be injected through the same nozzle inlet port using a metering pump.

A second method of accomplishing the above may be to apply a vacuum to the manifold 36, rather than applying pressure to entrance passage 24. The vacuum source may be a Venturi type blower with a trap, or a pump. The sealed volume 25 may be sealed or vented using one or more of the exit passages 26 as vents.

In operation, lenses were normally processed using 30 psig pressure (without retainer) or 40 psig (with retainer) on the above described entrance passage 24 for one to two seconds, and preferably 1.1 seconds.

After the removal of the deionized water, the packages are dosed with 0.95–1 ml of saline solution and allowed to equilibrate in a sealed package for osmolality.

Lenses removed with apparatus described herein have been inspected and found to have suffered no deleterious effects from the solution removal operation described above. It was also found that longer periods for injection of pressurized air at the above pressure and rate were not effective to remove all visible water residue. Prior to dosing with the saline solution, the amount of residual water was ascertained and found to be between 0.0110 and 0.0122 grams which corresponds to a 1.1 to 1.2 weight % dilution in the subsequent 1.0 ml saline dosing.

As is readily apparent, variations in the above apparatus and method are possible without departing form the invention which is precisely delineated by the claims that follow.

We claim:

1. An apparatus for removal of a liquid from a container having a bowl portion and a flange portion, said bowl portion containing said liquid and a hydrophilic ophthalmic lens, said apparatus comprising:

a nozzle having a central face with a shoulder about a circumferential periphery of said central face, said central face having therethrough at least one fluid entrance orifice and at least one fluid exit orifice defined therein, said shoulder including a sealing means, said sealing means sized to engage said flange portion of said container and position said central face above the ophthalmic lens carried in said bowl, a resilient lens retainer for urging said ophthalmic lens into engagement with said bowl during removal of said liquid, a source of purging fluid connected to said entrance orifice, said source having a pressure and flow sufficient to remove substantial all of said liquid, said orifices defined by said nozzle face located in an arrangement which distributes the flow of said purging fluid and said liquid in a substantially symmetric manner about the center axis of the lens.

2. The apparatus of claim 1 wherein said lens retainer is formed of silicon elastomer.

3. The apparatus of claim 2 wherein the entrance orifice is located along a central axis of the nozzle and a plurality of exit orifices are symmetrically arranged between the entrance nozzle and the said sealing means.

4. The apparatus of claim 3 wherein said nozzle further includes a bias means for applying a separation force to the flange of said package when said nozzle is retracted.

5. The apparatus of claim 3 wherein said lens retainer includes a plurality of arms that are symmetrically spaced with respect to said orifices.

6. The apparatus of claim 5 wherein said lens retainer further includes a central orifice coaxially aligned with said entrance nozzle.

7. The apparatus of claim 5 wherein said lens retainer further includes a central hub supported by said plurality of arms, said hub having at least one nub thereon for engaging said ophthalmic lens during removal of said liquid.

8. The apparatus of claim 1 wherein said silicon elastomer has a durometer hardness of 70A.

9. The apparatus of claim 1 wherein the purging fluid is a gas.

10. The apparatus of claim 1 wherein the purging fluid is a saline solution.

11. A method of removing a liquid from a container having a bowl portion and a flange portion, said bowl portion containing said liquid and a hydrophilic ophthalmic lens, said method comprising:

forming a sealed volume above said container bowl, said volume including a volume defined by said bowl, resiliently biasing said ophthalmic lens into engagement with said bowl, introducing purging fluid through an entrance passage into said sealed volume in a substantially symmetric manner about the center axis of the lens such that there is no migration of the lens, at a pressure and with a flow sufficient to remove substantially all of said liquid, removing substantially all of said purging fluid and liquid from said sealed volume through an exit passage.

12. The method of claim 11 wherein said purging fluid is introduced along the central axis of said ophthalmic lens and said liquid and said purging fluid are removed in a symmetric flow at a plurality of equally space locations between the center axis of said lens and the periphery of said sealed volume.

13. The method of claim 12 wherein said resilient biasing step occurs as the volume is defined and sealed.

14. The method of claim 13 wherein said lens is resiliently urged into engagement with said bowl by a lens retainer.

15. The method of claim 14 wherein said flow of liquid and purging fluid is also symmetric about said lens retainer.

16. The method of claim 11 wherein said purging fluid is air, and the liquid remaining after said purging step is less than 0.02 grams.

17. The method of claim 16 wherein said air is pressurized to 50 psig and said bowl is purged for less than 5 seconds.

18. The method of claim 16 wherein said introduction of purging fluid is sufficiently rapid to cause pressurization of said sealed volume.

19. The method of claim 18 wherein the forming of a sealed volume seals the liquid in the bowl portion and prevents deposit of liquid on said flange during said purging or the removal of said purging fluid and liquid.

20. The method of claim 11 wherein a plurality of lenses, with each lens of said plurality in a separate bowl, is simultaneously purged by an array of nozzles.

* * * * *